United States Patent [19]

Soto

[11] 4,078,699
[45] Mar. 14, 1978

[54] FLEXIBLE PACKAGE WITH FLUID-PRESSURE SEALING DISPENSER

[75] Inventor: Ricardo Hurtado Soto, Bogota, Colombia

[73] Assignee: Steriflex Packaging Co., Bohemia, N.Y.

[21] Appl. No.: 696,737

[22] Filed: Jun. 16, 1976

Related U.S. Application Data

[63] Continuation-in-part of Ser. No. 543,264, Jan. 23, 1975, abandoned.

[51] Int. Cl.$^2$ .............................................. A61M 5/14
[52] U.S. Cl. ................................. 222/89; 128/214 D; 128/272; 206/532
[58] Field of Search ..................... 222/80, 81, 89, 541; 229/66; 206/219, 222, 530, 532; 128/DIG. 24, 214 D, 272

[56] References Cited

U.S. PATENT DOCUMENTS

| 2,986,142 | 5/1961 | Bieberdorf et al. | 222/81 X |
| 3,239,104 | 3/1966 | Scholle | 222/81 |
| 3,255,923 | 6/1966 | Soto | 222/80 |
| 3,474,789 | 10/1969 | Soto | 128/272 |
| 3,589,595 | 6/1971 | White | 229/66 |

FOREIGN PATENT DOCUMENTS

| 830,222 | 3/1960 | United Kingdom | 222/81 |
| 1,417,397 | 12/1975 | United Kingdom | 222/89 |

Primary Examiner—Robert B. Reeves
Assistant Examiner—David A. Scherbel
Attorney, Agent, or Firm—Ostrolenk, Faber, Gerb & Soffen

[57] ABSTRACT

A package includes a closed pouch-type container of flexible material with fluid contents. One portion of the container is formed into a pocket for sealingly receiving a dispenser assembly. When assembled to the container, an insert conduit penetrates the innermost portion of the pocket and communicates with the contents of the container for dispensing the same.

16 Claims, 15 Drawing Figures

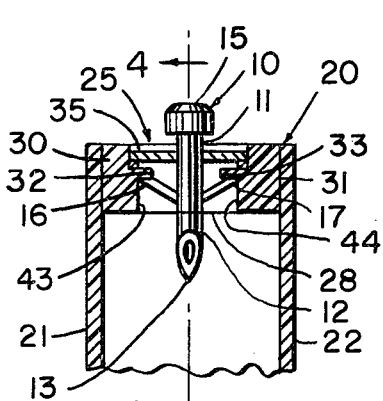
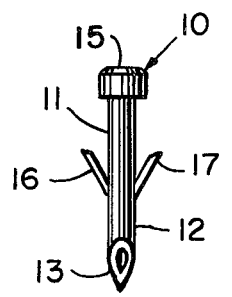
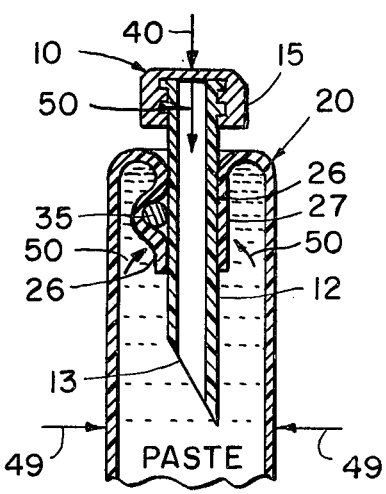
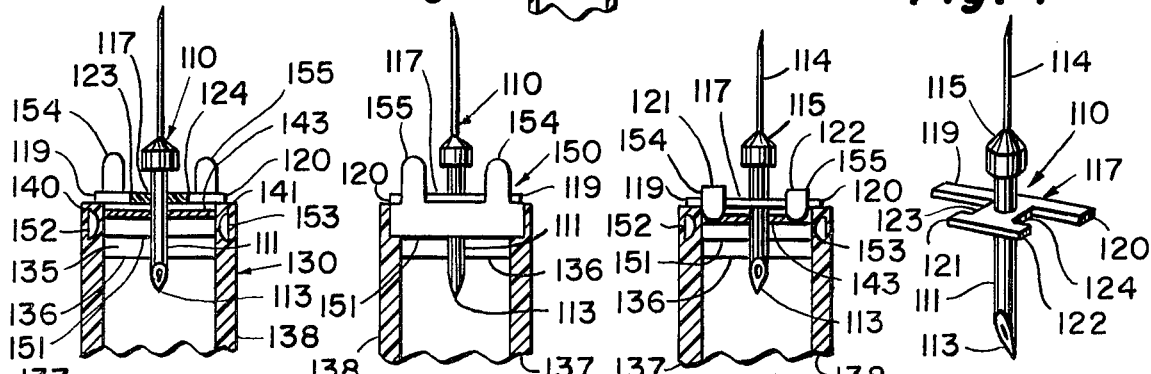
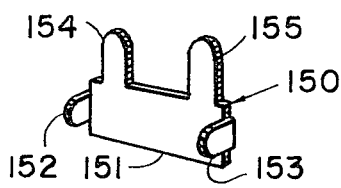
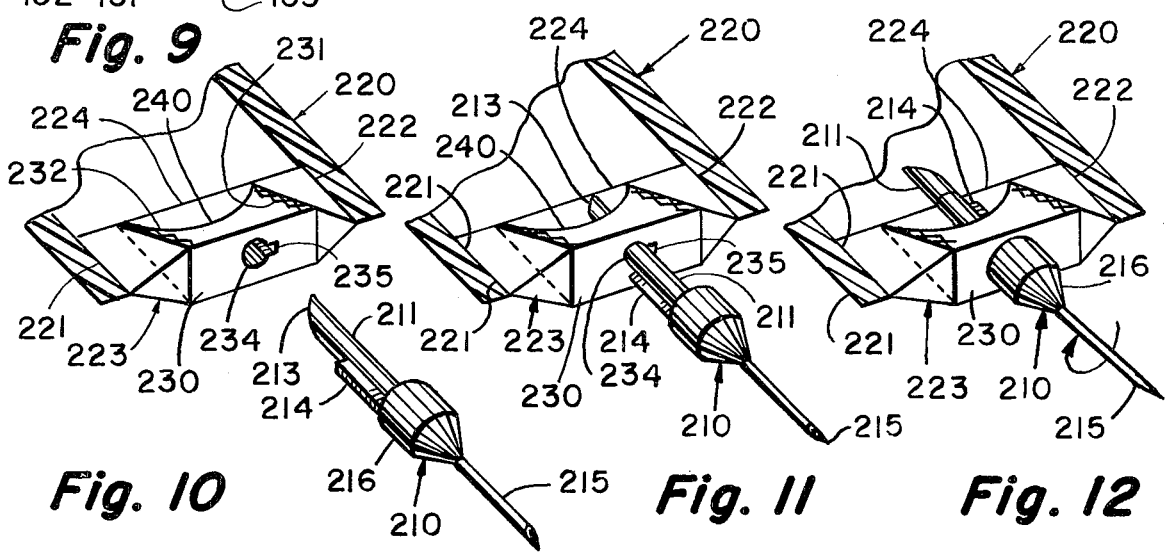

FLEXIBLE PACKAGE WITH FLUID-PRESSURE SEALING DISPENSER

RELATED APPLICATION

This is a continuation-in-part application of copending application Ser. No. 543,264, filed Jan. 23, 1975, now abandoned for "Flexible Package with Counter-Pressure Dispenser".

BACKGROUND AND SUMMARY

The present invention relates to apparatus for storing and dispensing medicaments, foods or the like, and more particularly, it relates to a sealed container for fluids and a separate attachable dispenser assembly for use with it. The word "fluid" is intended in the broad sense of any flowable substance, including liquids, pastes, gels, etc.

The package of the present invention includes a sealed collapsible container of puncturable thin film material with fluid contents. One portion of the container is formed into a pocket. The container is also provided with structure for attachably receiving a dispenser assembly. The dispenser assembly includes a specially designed cannula with an insert or penetration conduit.

In assembling the dispenser to the container, the insert conduit is placed in the pocket and forced to penetrate the innermost portion thereof. The body of the dispenser is secured to the receiving structure of the container. When pressure is applied to the container and its contents, the fluid pressure forces the inner folds of the pocket into progressive sealing engagement with the insert conduit of the cannula to prevent spillage or seepage of the liquid contents around the cannula.

Means are provided in the container to separate the folds of the pocket to facilitate insertion of the insert conduit. Means are also provided to stiffen the container adjacent the pocket so that it does not collapse during assembly or use.

One of the important features of the present invention is the means by which the inner folds of a thin film pocket sealingly engage the insert conduit of a dispenser assembly after it penetrates the innermost portion of the pocket. As hand pressure is applied to the container and contents, fluid pressure will cause the inner folds of the pocket to wrap around and sealingly engage the insert conduit of the dispenser to prevent seepage through the pierced portion of the pocket. As the pressure is increased on the contents, the contact area between these inner folds and the insert conduit and the sealing force will increase progressively, thereby preventing seepage or loss through the puncture aperture. Pressures over 15 p.s.i. can be applied to the container.

Another feature of the present invention is that the dispenser assembly is axially located at an edge of the container. This facilitates the complete withdrawal of the fluid contents and the pressing operation on the container. That is, the container can be squeezed at one end, thence progressively toward the dispenser assembly until all contents are removed.

Another feature is the warranty that the container has not been opened until it is perforated for use.

Still another feature is that when the container is perforated, it can be used as a reusable multi-dose package until all the contents have been drained.

An advantage of the invention is that it becomes feasible to provide large reusable, collapsible containers with the aforesaid features at a very low cost. Still another advantage is the use of the flexible container walls as a pressuring element to dispense the contents, e.g., liquids, pastes, waxes, etc., under positive pressure.

Other features and advantages will be apparent to persons skilled in the art from the following detailed description of preferred embodiments accompanied by the attached drawing wherein identical reference numerals will refer to like parts in the various views.

THE DRAWING

FIG. 1 is a fragmentary side view of a first embodiment of the invention with the dispenser assembled to the container;

FIG. 2 is a frontal view of the dispenser of FIG. 1;

FIG. 3 is a fragmentary transverse cross sectional view of the container of FIG. 1;

FIG. 4 is a cross sectional view taken through the sight line 4—4 of FIG. 1;

FIG. 5 is a fragmentary front view of a second embodiment of the invention with the dispenser assembled to but not secured to the container;

FIG. 6 is a rear view of the apparatus of FIG. 5;

FIG. 7 is a view similar to FIG. 5 with the dispenser assembled and secured to the container;

FIG. 8 is a perspective view of the dispenser assembly of the embodiment of FIG. 5;

FIG. 9 is a perspective view of the container stiffening element of the embodiment of FIG. 5;

FIG. 10 is a fragmentary perspective view of a third embodiment of the invention with the dispenser assembly separated from the container;

FIG. 11 is a view similar to FIG. 10 with the dispenser assembly partially assembled to the container;

FIG. 12 is a view similar to FIG. 10 with the dispenser assembly fully assembled to the container;

DETAILED DESCRIPTION

Figures 13, 14, 15:
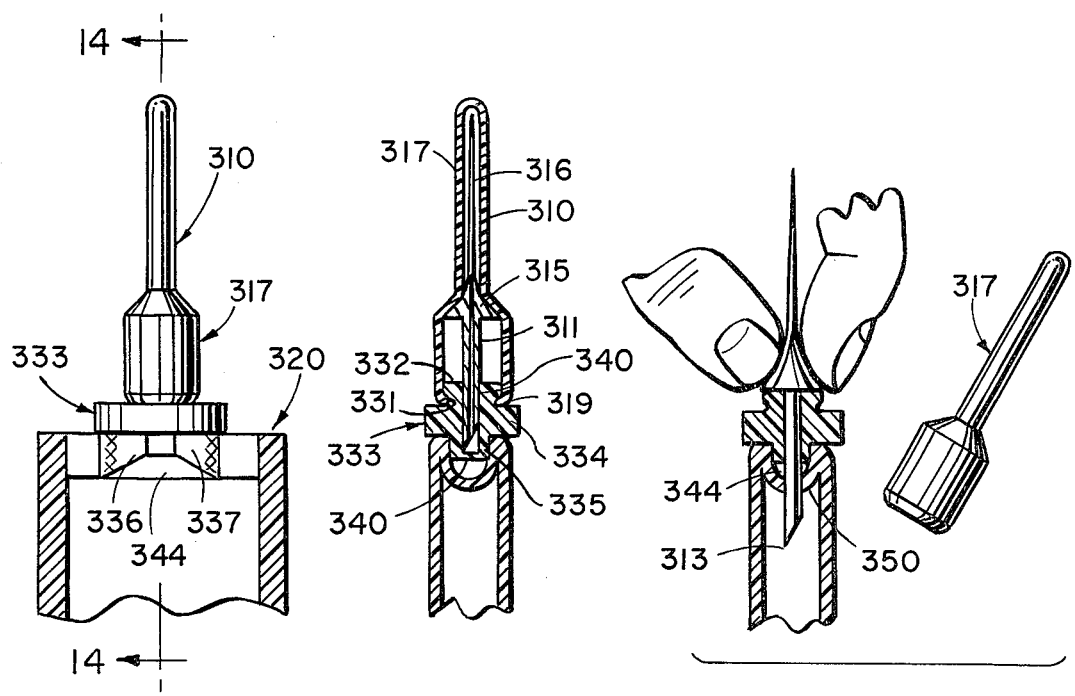
FIG. 13 is a fragmentary front view of a fourth embodiment of the invention.
FIG. 14 is a vertical cross sectional view taken through the section line 14—14 of FIG. 13.
FIG. 15 is also a vertical cross sectional view, with the needle protector removed, and illustrating insertion of the needle.

Turning first to the embodiment of FIGS. 1-4, reference numeral 10 generally designates a dispenser assembly in the form of a cannula. The dispenser assembly 10 includes an elongated tube 11, the lower portion of which is designated 12 and forms an insert conduit. The tip of the insert conduit 12 is cut on an incline 13 to form a point to facilitate penetration. The top of the tube 11 is provided with exterior threads for receiving internally threaded cap 15.

Extending outwardly from the sides of the tube 11 and integral therewith are first and second projections for barbs 16 and 17. The barbs 16, 17 form a general V shape tapering in the direction of insertion of the dispenser assembly. Preferably the dispenser assembly is made of plastic so that the barbs 16, 17 are slightly flexible and may be pressed inwardly—that is, toward the tube 11—during insertion.

The dispenser assembly 10 is adapted to be assembled to a container generally designated by reference numeral 20 in the form of a sealed bag or pouch. Preferably, the container 20 is made from thin film material which is thermoplastic so that the sides may be heat sealed at 21, 22. The top of the container 20 is folded inwardly to form a pocket 25 having first and second sides 26, 27 which are joined at an innermost portion or fold 28 (see FIGS. 1 and 3).

As best seen in FIG. 1, the sides of the container adjacent the pocket 25 is also heat sealed at 30 and 31, and inwardly extending teeth are formed respectively at 32 and 33. A separating filament 35 extends across the mouth of the pocket 25 and is secured at its ends by being embedded respectively in the heat-sealed portion 30, 31 of the container adjacent the pocket 25. The function of the filament 35 is to maintain the sides 26, 27 of the pocket 25 in slightly spaced relation to facilitate insertion of the dispenser assembly 10.

When it is desired to dispense the contents of the package, the dispenser 10 is inserted in the direction of the arrow 40 in FIG. 4 so that the tip 13 penetrates the innermost fold 28 of the pocket 25, whereby the tube 11 communicates with the fluid contents of the package.

When the dispenser 10 is thus inserted, the outermost ends of the barbs 16, 17 are trapped respectively beneath the teeth 32, 33 in the container; and this serves two purposes. First, the outward extension of the barbs 16, 17 is only slightly less than spacing of the edges 43, 44 of the pocket at this location. Hence, the barbs 16, 17 hold the pocket in an extended position, thereby providing some stiffening means for the pocket. Secondly, because the barbs 16, 17 are trapped beneath the teeth 32, 33, the dispenser 10 is secured to the container and cannot be accidentally dislodged. Preferably, the filament 35 is colored red or other easily perceptible color so as to facilitate its location.

With the cap 15 sealing the dispenser (FIG. 4), any pressure (arrows 49) exerted on the package generates an internal pressure on the fluid in the direction of the arrows 50 causing a progressive sealing engagement between the sides 26, 27 of the pocket 25 and the outer surface of the insert conduit 12 thereby preventing the escape or seepage of the fluid contents through the penetration aperture and giving a permanent sealing to the package. With cap 15 removed, part of the contents can be dispensed and the package can be closed again by securing the cap 15 which acts as a reclosing element. Other reclosing elements can be used, such as a pressure cap or any other conventional reclosing device.

Turning now to the embodiment of FIGS. 5-9, the dispenser assembly is generally designated by reference numeral 110 (seen best in FIG. 8), and it includes an insert conduit 111 which is again inclined at 113 to form a point for insertion. The upper end of the conduit 111 is provided with a needle 114 secured by means of an adapter 115.

A harness 117 is secured to the upper portion of the insert conduit 111. The harness 117 includes first and second elongated bars 119, 120 and first and second stub bars 121, 122. The elongated bar 119 and stub bar 121 are separated to form a guide 123. Similarly, the elongated bar 120 and stub bar 122 are separated to form a guide or slot 124.

Referring now to FIG. 5, the container is generally designated by reference numeral 130, and it includes a pocket 135 at the upper edge thereof. The innermost portion of the pocket 135 is designated 136. The sides of the container 130 are heat sealed together at 137, 138; and the upper portions thereof, adjacent the pocket 135 are provided with slits 140, 141. Further, a separator filament or thread 143 is provided adjacent the mouth of the pocket 135, the ends of the filament 143 being held by the upper portions of the heat-sealed container margins 137, 138.

A stiffener element generally designated 150 in FIG. 9 includes a horizontally elongated body 151, to the sides of which are appended tabs 152, 153. Extending upwardly from the body 151 are a second set of tabs 154, 155. The side tabs 152, 153 are in register with the slits 140, 141 in the margins of the container. Preferably, the stiffener element 150 is made of a bendable metal such as aluminum. When the tabs 152, 153 are inserted in the slots 140, 141, the tabs may be bent inwardly as seen in FIG. 5 so that the stiffener element is secured to the container.

The upwardly extending tabs 154, 155 are spaced at a distance so as to be received in the grooves 123, 124 of the dispenser assembly 110 (compare FIGS. 5 and 6). When thus received, the tabs 154, 155 are bent over to engage the longer bars 119, 120 on the harness 117 of the dispenser assembly, as best seen in FIG. 7. This secures the dispenser assembly to the container while, at the same time, stiffening the sides of the container adjacent the pocket 135. The dispenser assembly 110 is inserted with the point 113 leading so as to penetrate the innermost edge 136 of the pocket 135, as in the case of the embodiment of FIG. 1.

Once the dispenser assembly is assembled to the container by means of the stiffening element 150, the dispensing of the contents of the container operates as in the previously discussed embodiment. That is to say, when the container is squeezed, the pressure induced on the fluid contents causes the sides of the pocket 135 to effect a progressive sealing engagement with the insert conduit 111. During insertion of the dispenser assembly, the upstanding tabs 154, 155 act as a guide for the insertion of the dispenser assembly.

Turning now to the embodiment of FIGS. 10-12, the dispenser assembly is generally designated by reference numeral 210, and the container 220. The dispenser assembly 210 again includes an insert conduit 211 which is tipped at 213. Adjacent the conduit 211 is a spline or key 214. A needle 215 is secured to the conduit 211 by means of an adapter 216.

The container 220 has its marginal edges heat sealed at 221, 222. A pocket 223 is formed at the dispensing end of the container 220. The pocket 223 is partially defined by an innermost edge 224. The pocket 223 extends between the marginal edges 221, 222.

A generally wedge-shaped separator element 230 is located in the pocket 223, and heat sealed to the sides of the pockets along the locations 231, 232. The separator element 230 includes a central bore 234 which is sized to receive the insert conduit 211, and a slot 235 which is adapted to receive the key 214 of the dispenser assembly. The separator element 230 serves as a stiffener for the pocket.

Turning now to FIG. 11, the innermost portion of the separator 231 is removed to form a cavity 240. This permits the inner sides of the pocket 223 to form the progressive sealing engagement with the insert conduit 211 when it is fully inserted (FIG. 12) and the container is squeezed.

To assemble the dispenser 210 to the container, the insert conduit 211 is aligned with the bore 234 (the inclined edge 213 may be used as a guide). When the dispenser is inserted to the position shown in FIG. 11, it is rotated until the key 214 is aligned with the slot 235; at which time, the dispenser is fully inserted to the position shown in FIG. 12, the insert conduit penetrating the innermost edge 224 of the pocket 223. This embodiment of the invention permits the combination of the container and dispenser to be a single unit for shipment or storage.

Turning now to the embodiment of FIGS. 13-15, there is shown a modification of the invention in which the dispenser assembly includes a sterile needle.

In FIG. 13, a dispenser assembly is generally designated by reference numeral 310, and the container 320. The dispenser assembly 310 includes an insert conduit 311 which is sharpened at 313 to provide a penetration point. Again, the insert conduit is tubular. At the upper end of the insert conduit is a conical portion 315, at the upper end of which is a needle 316.

A cover 317 is provided for the dispenser assembly 310, and it generally conforms to the shape of the dispenser assembly. At the lower portion of the cover element, there is an inwardly extending lip 319 which is received in a corresponding groove 331 of a collar 332 on a stiffener element generally designated 333. The stiffener element 333 includes a central expanded body portion 334, a lower, central well 335, and outwardly extending flanges 336, 337. The bag or container 320 is heat sealed to the flanges 336, 337, as indicated by the heat-sealing lines in FIG. 13.

A central bore 340 is formed through the collar 332, the body 334, and partially into the well 335 for receiving the sharpened end of the insert conduit 311, as seen in FIG. 14. This leaves a lower, thin membrane 340 which is easily penetrated by the sharpened insert conduit. The shape of the sealing flanges 336, 337, as best seen in FIG. 13, is such as to leave a cavity at 344 so that the walls of the pocket may sealingly engage the insert conduit after it penetrates the membrane 340 and the pocket, as seen in FIG. 15.

In operation, the cover is removed by pulling it off, and the fingers are used to engage the conical surface 315, and push the insert conduit through the membrane 340 and the innermost portion of the pocket 350. The advantage of this embodiment is that the parts may be sterilized using gas sterilization, for example, and when they are assembled as seen in FIG. 13, 14, the dispenser assembly as well as the contents of the container will remain in a sterilized condition until it is desired to use the contents of the package.

Having thus disclosed in detail preferred embodiments of the invention, persons skilled in the art will be able to modify certain of the structure which has been illustrated or to substitute equivalent elements for those disclosed while continuing to practice the principle of the invention. In particular, other suitable sealing means, dispensing assemblies, reclosure elements, and covers may be used, other than those described above, depending upon the intended function of the package and its contents. It is, therefore, intended that all such modifications and substitutions be covered as they are embraced within the spirit and scope of the appended claims.

I claim:

1. In a package for containing and dispensing fluid contents, said package comprising a closed, sealed, collapsible container of puncturable, flexible material, said container having an edge and having a dispensing location adjacent said edge thereof, a portion of said container adjacent said dispensing location being double folded at folds adjacent said edge to provide two inner plies, said plies being joined at a fold along an innermost edge of said pocket, which extends into said container, for defining a channel-shaped pocket between said plies; and dispenser means securable to said container, and including an insert conduit for insertion between said plies of said pocket for penetrating said innermost edge thereof, the improvement comprising means for stiffening said container adjacent said folds at said container edge to maintain the shape of said pocket; separator means interposed between said plies of said pocket for holding said plies in spaced relation; said insert conduit being insertable past said separator means;

pressure exerted on said container after insertion of said dispenser means will be transmitted to said plies of said pocket to force the same together in progressive sealing engagement with said insert conduit to prevent seepage of the contents.

2. In the package of claim 1, said container having marginal edges which are sealed together, the improvement further comprises said container supporting teeth at opposite ends of said pocket, and projecting toward the other said end of said pocket, said dispenser means including a pair of barbs extending outwardly of said insert conduit a total distance further than the spacing between said teeth whereby when said dispenser means is assembled to said container, said barbs pass over said teeth and are thereafter secured beneath said teeth preventing removal of said dispenser means.

3. In the package of claim 2, the improvement further comprises the lateral extension of said pocket between its said ends and beneath said teeth in said container approximates the lateral extension of said barbs in said assembled relation to said container, said barbs acting to provide said stiffening means to maintain the shape of said pocket.

4. In the package of claim 2, the improvement further comprises said separator means includes a filament extending lengthwise adjacent the mouth of said pocket and secured at said ends of said pocket.

5. In the package of claim 2, the improvement further comprising said barbs defining a V-shape between them and said dispenser means being assembled to said container with the apex of the V-shape extending into said container.

6. In the package of claim 1, the improvement further comprises said dispenser means includes a reclosing member received on the distal end of said insert conduit.

7. In the package of claim 1, the improvement further comprises said stiffening means comprises a a body, gripping means for securing said body to said container, whereby said body engages and thereby stiffens said container, and tab means extending from said body for attaching to said dispenser means.

8. In the package of claim 7, the improvement further comprises said dispenser means further includes a harness secured to said insert conduit, said harness defining first and second side grooves aligned to receive said tab means of said stiffening means when said dispenser means is assembled to said container, whereupon after assembly, said tab means may be folded over to securely engage and hold said harness.

9. In the package of claim 7, the improvement further comprising said stiffening means body being comprised of a piece of bendable metal and said tab means extending upwardly of said body.

10. In the package of claim 1, the improvement further comprises said stiffening means and said separating means comprise a generally wedge-shaped element secured to said container within said pocket, said element having a reduced thickness from the mouth of said pocket to the innermost edge thereof, a bore defined in and extending through said element toward said reduced thickness end thereof for receiving said insert conduit, said element being shaped to define a cavity adjacent the location of penetration of said pocket by said insert conduit to permit the plies of said pocket to engage said insert conduit.

11. In the package of claim 10, the improvement further comprises said dispenser means further comprises an elongated key member extending along said insert conduit, and said wedge-shaped element includes a slot communicating with said bore and adapted to receive said key of said dispenser means when said dispenser means is being assembled to said container in dispensing relation.

12. In the package of claim 1, the improvement further comprises said stiffening means and said separating means comprise a generally wedge-shaped element secured to said container within said pocket, said element having a reduced thickness from the mouth of said pocket to the innermost edge thereof, a bore defined in an extending through said element toward said reduced thickness end thereof for receiving said insert conduit.

13. In a package for containing and dispensing fluid contents, said package comprising a closed, sealed, collapsible container of puncturable, flexible material, said container having an edge and having a dispensing location adjacent said edge thereof, a portion of said container adjacent said dispensing location being double folded at folds adjacent said edge to provide two inner plies, said plies being joined at a fold along an innermost edge of said pocket, which extends into said container for defining a channel-shaped pocket between said plies; and dispenser means securable to said container, the improvement comprising rigid means defining a bore therethrough and interposed between said plies of said pocket for holding said plies in spaced relation and for stiffening said container adjacent said folds to maintain the shape of said pocket; said dispenser means including an insert conduit for insertion through said bore of said rigid means between said plies of said pocket for penetrating said innermost edge thereof, whereby pressure exerted on said container after insertion of said dispenser means will be transmitted to the plies of said pocket to force the same together in progressive sealing engagement with said insert conduit to prevent seepage of the contents.

14. In the package of claim 13, the improvement further comprises said dispenser means further comprises a body portion that is larger than said bore and is adjacent said insert conduit for engaging said rigid means and for limiting the insert motion of said dispenser means, said body portion providing a finger-engaging surface to facilitate insertion by pushing.

15. In the package of claim 14, the improvement further comprises said dispenser means further comprises a needle extending from said finger-engaging surface.

16. In the package of claim 15, the improvement further comprises said dispenser means is sterile and sealed, and includes a membrane sealing said bore but pierceable by said insert conduit; and cover means removably coupled to said rigid means for enclosing said body portion and needle of said dispenser means.

* * * * *